United States Patent [19]
Langer et al.

[11] Patent Number: 5,484,576
[45] Date of Patent: Jan. 16, 1996

[54] FIXED BED REACTORS HAVING A SHORT CATALYST BED IN THE DIRECTION OF FLOW

[75] Inventors: Reinhard Langer; Hans-Josef Buysch, both of Krefeld; Paul Wagner, Düsseldorf, all of Germany

[73] Assignee: Bayer Aktiengesellschaft, Leverkusen, Germany

[21] Appl. No.: 26,329

[22] Filed: Mar. 4, 1993

[30] Foreign Application Priority Data

Mar. 12, 1992 [DE] Germany ......................... 42 07 905.5

[51] Int. Cl.[6] ...................................................... B01J 8/02
[52] U.S. Cl. .......................... 422/211; 422/192; 422/198
[58] Field of Search .................................. 422/198, 202, 422/190, 192, 193, 196, 197, 211, 201

[56] References Cited

U.S. PATENT DOCUMENTS

| | | | |
|---|---|---|---|
| 1,826,548 | 10/1931 | Jaeger | 422/202 |
| 2,078,947 | 5/1937 | Houdry et al. | 422/200 |
| 2,433,670 | 12/1947 | Kropp | 422/188 |
| 3,128,242 | 4/1964 | Bergstrom et al. | 208/65 |
| 4,242,525 | 12/1980 | Kiyoura | 562/577 |
| 4,732,918 | 3/1988 | Lohmueller et al. | 422/201 |
| 4,896,704 | 1/1990 | Aly et al. | 422/216 X |
| 4,946,657 | 8/1990 | Zardi | 422/218 X |
| 5,149,884 | 9/1992 | Brenner et al. . | |

FOREIGN PATENT DOCUMENTS

| | | |
|---|---|---|
| 0244632 | 11/1987 | European Pat. Off. . |
| 0297474 | 1/1989 | European Pat. Off. . |
| 0416710 | 3/1991 | European Pat. Off. . |
| 1296614 | 5/1962 | France . |
| 1297766 | 5/1962 | France . |
| 942805 | 10/1956 | Germany . |
| 2929300 | 1/1981 | Germany . |
| 3414717 | 10/1985 | Germany . |
| 3612213 | 10/1987 | Germany . |
| 2132111 | 7/1984 | United Kingdom . |
| 88/03915 | 6/1988 | WIPO . |

OTHER PUBLICATIONS

Chemical Abstracts, vol. 52, 14247, Ger. 942,805.
Ullmanns, Enzyklopadie der technishen Chemie (Encyclopedia of Industrial Chemistry), 4th Edition, vol. 3, pp. 465–469.
Kirk–Othmer, Encyclopedia of Chemical Technology, vol. 19 (f1982), pp. 880–914.
Chemie–Ingenieur–Technik 51 (1979), pp. 257–265.
Chem. Tech. 30 (1978), 74.

Primary Examiner—James C. Housel
Assistant Examiner—Rachel Heather Freed
Attorney, Agent, or Firm—William C. Gerstenzang; Sprung Horn Kramer & Woods

[57] ABSTRACT

Reactors are described for the continuous reaction of gaseous substances on fixed bed catalysts with continuous temperature control and with the aid of a heat transport medium. These reactors are characterised by the design of the catalyst bed in the form of one or more regularly shaped sheet-like layers having a thickness of 0.01–50 cm, the surface of the catalyst layers being covered by a gaspermeable layer and this surface, on the starting material intake side and/or on the product outlet side, facing a likewise regularly shaped wall at a distance of 0.1 to 10 cm, which wall separates the space for the substances to be reacted or reacted substances from the space for the heat transport medium. The reactors are further characterised by the substances to be reacted being directed so as to flow through the catalyst bed approximately or completely perpendicularly to the sheet-like catalyst layers.

12 Claims, 8 Drawing Sheets

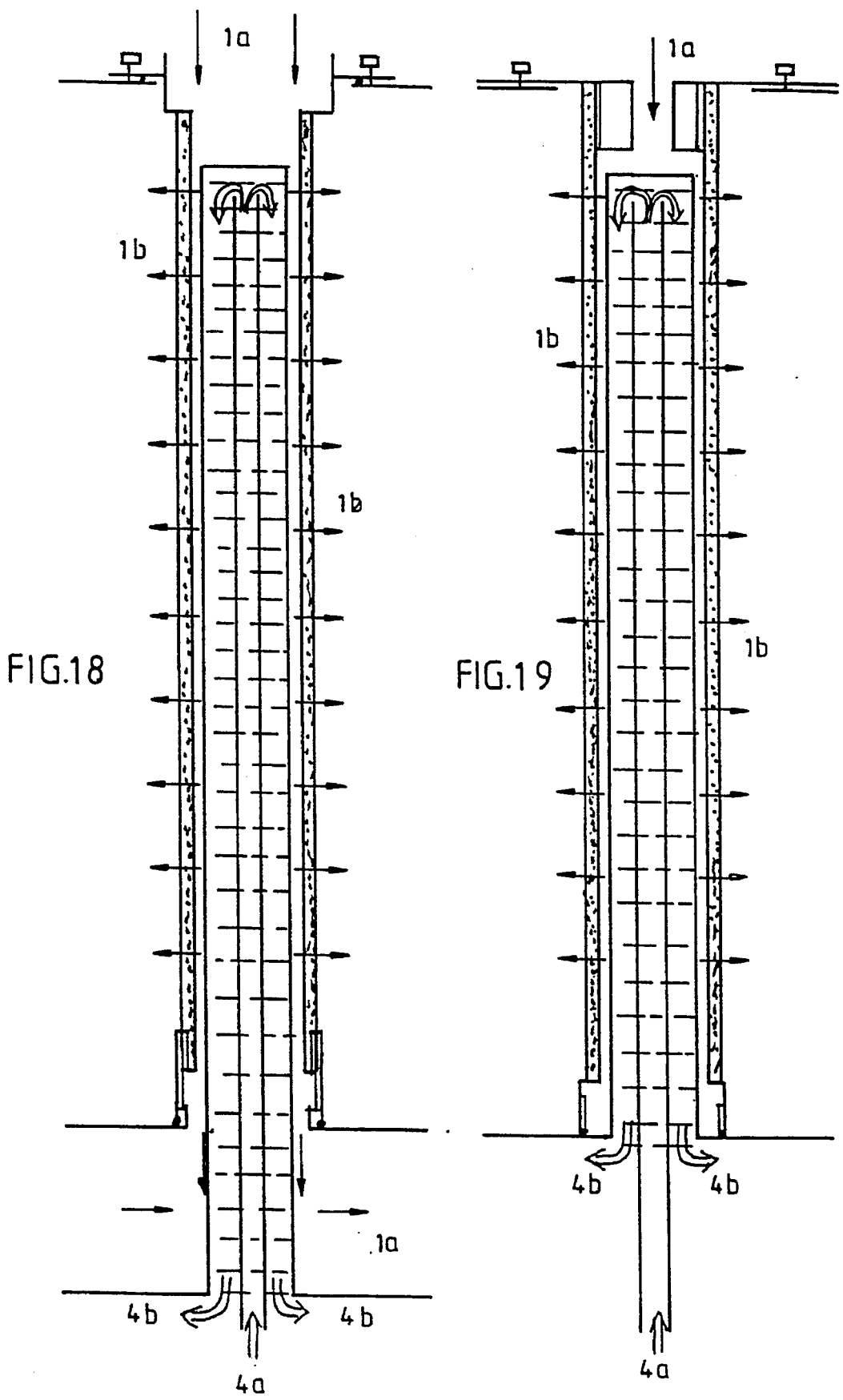

FIXED BED REACTORS HAVING A SHORT CATALYST BED IN THE DIRECTION OF FLOW

BACKGROUND OF THE INVENTION

1. Field of the Invention

The invention relates to fixed bed reactors for the reaction of gaseous starting materials or mixtures of starting materials which are characterised in that the starting materials or mixtures of starting materials flow through a catalyst bed, which is designed as a sheet, approximately or completely perpendicularly to these surfaces.

In this case it is possible to allow the function which describes the temperature and the starting material load in relation to position in the catalyst bed to have as flat a course as possible, as a result of which partial overloads and—especially in the case of highly exothermic reactions—temperature peaks are avoided.

These characteristics of the reactors according to the invention result in optimal selectivities and operating lives of the catalyst.

The invention further relates to the use of such fixed bed reactors for the reaction of gaseous starting materials or mixtures of starting materials.

The catalytic reaction of gases on stationary catalysts can easily be carried out as a continuous process and has the attractive convenience that the product does not generally have to be separated from auxiliaries, such as solvents or catalysts. Accordingly, preference is being given in the chemical industry to production of chemicals having medium and large production quantities in this way.

Many organic compounds are significantly more stable in the gaseous state of matter than in the liquid state, since, because of the low spatial concentration, bimolecular and higher molecular side reactions are repressed, so that, for example, highly exothermic reactions can be carried out at a higher temperature level than in the liquid state, which is in turn advantageous for coupled thermal energy recovery.

Other reactions, for example, endothermic cleavage reactions, require particularly high temperatures and can virtually only be carried out in the gas phase, in particular in the case of sensitive starting materials and products.

2. Description of the Related Art

A multiplicity of reactor types are described in the literature (Ullmanns, Enzyklopädie der technischen Chemie [Encyclopaedia of Industrial Chemistry], 4th edition, Volume 3, pp. 468–469; Kirk-Othmer, Encyclopedia of Chemical Technology, Volume 19 (1982), pp. 880–914). In this case, a distinction is made between reactors having a controlled temperature profile and those having an uncontrolled temperature profile.

Reactors having an uncontrolled temperature profile are composed of a dumped catalyst packing or of a catalyst bed made of catalytically active shaped bodies in a vessel, insulated to a greater or lesser extent, and of simple geometry.

The enthalpy of reaction in such reactors is passed on to the product mixture; therefore these types of construction are termed adiabatic. The main attraction of these reactors is their simple, and thus cheap and easily-maintained, construction. However, when such adiabatic reactors having an uncontrolled temperature profile are used, account should be taken of the fact that chemical changes have an exponential character both with respect to kinetic and thermodynamic aspects and thus react very sensitively to temperature changes. This means that many reactions proceed with sufficient selectivity and at a sufficient rate in a narrow temperature range. The catalyst itself can also prove to be temperature-sensitive.

Since the majority of chemical reactions have a significant heat of reaction in relation to the thermal capacity of the systems, only in very few cases can the removal or supply of thermal energy to maintain the required temperature range be dispensed with (controlled temperature profile).

In the case of the reactors having a controlled temperature profile, a distinction is made between the continuous and the stepwise thermostatting, that is heat removal or heat supply. The stepwise thermostatting in principle breaks down an adiabatic reactor into part-sections, after leaving which the gas is brought into thermal interaction with a heat transport medium or receives an admixture of fresh starting material mixture at an appropriate temperature (Ullman, loc. cit., p. 473). In this type of reactor, the reaction should not be too thermally demanding since otherwise a very large number of stages is required in order to maintain the temperature limits. On the other hand, highly complicated reactor structures have been developed especially for the synthesis of ammonia and methanol for the optimal housing and optimal operation of a relatively large number of catalyst bed sections and heat exchangers in a high pressure chamber (EP 297,474, EP 333,757 and literature cited therein).

For reactions having extremely high heat of reaction and catalysts or reactions having extremely sensitive temperature behaviour therefore, continuous thermostatting is to be installed. In this case, the catalyst can be housed either between the tubes or in the tubes of a heat exchanger (Linde reactor according to German Offenlegungsschrift 3,414,717 or tube bundle reactor according to Chemie-Ingenieur-Technik 51 (1979), p. 257–265). Reactors of this type having tube diameters of one to several centimeters and tube lengths of 2–20 m have been prior art for a long time. Despite the constant heat flow in a radial direction, in strongly exothermic reactions a hot-spot forms in the reactor tubes, which is responsible for losses in selectivity or catalyst damage.

It has already been described to diminish the hot-spot by diluting the catalyst at the beginning of packing with inert material or by the reactor tubes at the inlet end having a lower diameter than at the outlet end (German Offenlegungsschrift 2,929,300; GB 2,132,111). It has furthermore been described to alleviate the lack of uniform thermostatting by shortening the tubes of the tube bundle reactor to 1–30 cm, preferably 5–20 cm (German Offenlegungsschrift 3,612,213, EP 244,632). The tubes of such a short-tube reactor have internal diameters of 0.5–3 cm, preferably 1–2 cm. The advantages of this short-tube reactor are described as follows:

Large specific cooling surface area and uniform streaming of the heat transport medium to the tubes from the side lead to a defined temperature distribution in the reactor tube, uniform lateral streaming of the heat transport medium to all tubes is intended to lead to a compact construction with maximum heat transfer; even in the case of fine-grain catalyst a low pressure drop is said to result in the tubes.

In EP 244,632 mentioned, in addition an association is made between tube length and residence time without considering this in more detail; the short tube with short residence time and good heat dissipation is described as expedient for highly exothermic reactions having high energy of activation and thermally unstable reactants and products. However, in this case, no attention is paid to the number of tubes which a short tube bundle reactor must accommodate, the tube length of which is shorter than that of a current reactor by a factor of 50–500, in order to make possible industrially relevant product flow rates. In order to substitute a reactor not infrequently to be encountered in industry having 10,000 tubes of conventional length, these would have to be 500,000 to 5 million short tubes built into the short tube bundle reactor. Just as little attention is paid to the uniform flow through this giant number of tubes or the manner in which this is to be ensured or the manner in which the tubes are to be filled. EP 244 632 mentioned is exclusively concerned with the residence time and the uniform thermostatting, since according to known teaching the superficial loading of a catalyst bed (1 of starting material mixture per $m^2$ of external surface area of the catalyst bed and hour) is generally not a particularly characteristic parameter for the properties of a heterogeneous catalysed gas-phase reaction.

SUMMARY OF THE INVENTION

The invention relates to reactors for the continuous reaction of gaseous substances on fixed-bed catalysts with continuous temperature control with the aid of a heat transport medium, which are characterised by designing the catalyst bed in the form of one or more regularly shaped sheet-like layers having a thickness of 0.01–50 cm, the surface of the catalyst layers being covered by a gas-permeable layer and this surface, on the starting material intake side and/or on the product outlet side, facing a likewise regularly shaped wall at a distance of 0.1–10 cm, which wall separates the space for the substances to be reacted or reacted substances from the space for the heat transport medium and are characterised by the substances to be reacted being directed so as to flow through the catalyst bed approximately or completely perpendicularly to the sheet-like catalyst layers.

The invention further relates to the use of the reactors according to the invention in processes for catalysed thermally controlled gas-phase reactions having high endothermic or exothermic heat of reaction.

BRIEF DESCRIPTION OF THE DRAWINGS

The accompanying drawings show the principal construction and the principal mode of operation of the reactors according to the invention and some conceivable industrial embodiment variants. (FIG.1–FIG.19)

DETAILED DESCRIPTION OF THE INVENTION

Figure 1:
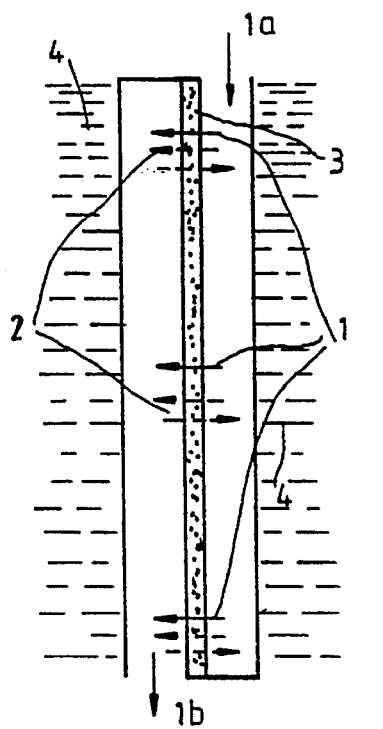

The reactors according to the invention enable the course of the function which describes the temperature and the starting material loading in relation to position in the catalyst bed to be as flat as possible. By this means, partial overloads and—especially in the case of highly exothermic reactions—temperature peaks are avoided. This enables side reactions resulting from catalyst overload or resulting from unsuitable catalyst temperature to be repressed, which benefits both the selectivity of the product preparation and the operating life of the catalyst. These advantages are achieved in the reactor according to the invention in that the catalyst bed has a particularly low extension in the direction of flow and also in that the heat of reaction is removed from the reaction zone or supplied to the reaction zone in parallel, antiparallel or parallel and antiparallel to the direction of flow of the substances through the catalyst bed. A further favourable effect of the low depth of penetration of such uniformly temperature-controlled and loaded catalyst beds is their low retention capacity for poorly volatile by-products, which additionally promotes extremely long catalyst operating lives. Thermostatting by means of a secondary heat circulation as an important industrial embodiment is principally considered below; however, it is also possible in principle to carry out direct steam thermostatting or another comparable direct thermostatting in the reactors according to the invention.

The fixed-bed reactors according to the invention permit a uniform loading and thermostatting of the catalyst used. A reactor according to the invention for largescale industrial uses nevertheless incorporates only a low number of internals which are, in addition, cheaply and easily maintained.

In the accompanying drawings, the arrows having continuous lines and the reference number (1) denote the particular mass flow from the feed of the starting material (1*a*) (starting substance/mixture of starting substances, if required together with a diluent or carrier gas) to the discharge of the product (1*b*) (reaction product/reaction mixture, if required with diluent/carrier gas).

The arrows having dashed lines and the reference number (2) denote the heat flow from the catalyst to the heat transport medium. In the accompanying drawings, dashed arrows, to illustrate the heat flows at the catalyst, show the case of an exothermic reaction. Endothermic reactions have a heat flux diametrically opposite to the arrow direction; such conditions are not explicitly considered in the drawings. The dotted, narrow surfaces (3) denote the catalyst bed covered by a gas-permeable layer; the gas-permeable layer is not particularly emphasised in the drawings. The horizontally dashed surfaces (4) denote the space, covered by a wall, for the heat transport medium. The heat transport medium is to be regarded as transported through the reactor according to the invention in a manner known to those skilled in the art and as connected to an external heater/cooler for the temperature control of endothermic/exothermic reactions. As is to be exemplified in the drawings, the heat transport medium stream is indicated by arrows having double lines and the reference number (4*a*) for the inlet and (4*b*) for the outlet.

Figure 2:
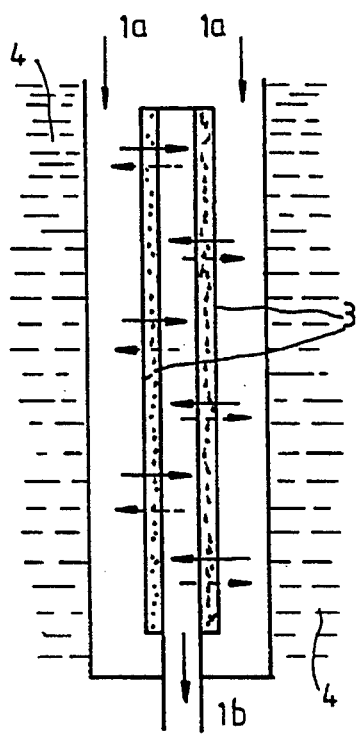
Figure 3:
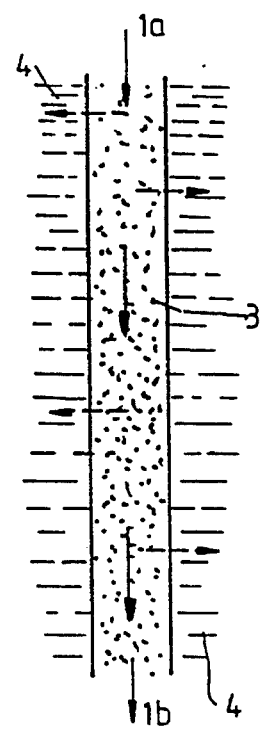

FIG. 1 shows the principle of the reactor according to the invention on the basis of a section through a planar, flat catalyst bed having opposite heat transport medium spaces; FIG. 2 shows the principle on the basis of a section through a catalyst bed designed as a hollow cylinder; FIG. 3 shows, in contrast hereto, a tube reactor according to the prior art, likewise in cross-section. Whereas in the reactor according to the invention the mass flow and heat flow always run in parallel, antiparallel or both in parallel and antiparallel to each other, in the conventional reactor, the mass flow and heat flow are orthogonal to each other. As a consequence, in the reactor according to the invention, the surfaces through which mass and heat flow are always identical, whereas they cannot be in the conventional reactor.

Figure 4:
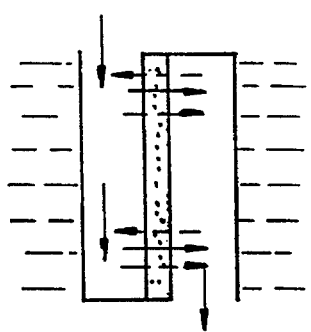
Figure 6:
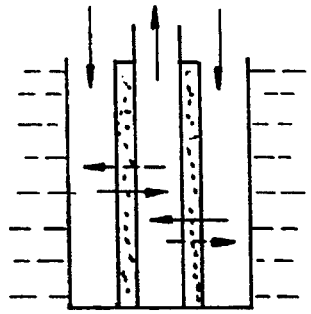
Figure 8:
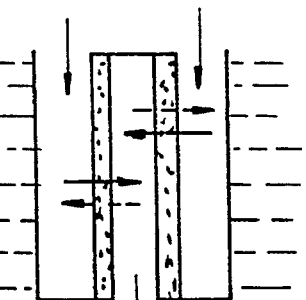
Figure 5:
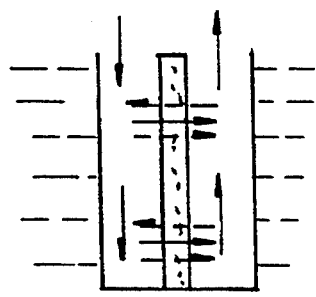
Figure 7:
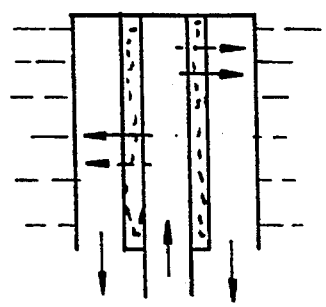
Figure 9:
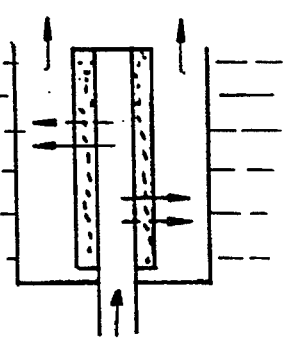

FIGS. 4–9 show variations of FIG. 1 and FIG. 2 in a modification of the structural design—flat catalyst bed or hollow cylinder as catalyst bed and feed and removal of starting material and product and necessity of energy supply or energy removal (in the case of endothermic or exothermic reaction)—a parallel or antiparallel direction of starting material stream to product stream is shown in the distribution layers and receiving layers and a parallel, antiparallel or both parallel and antiparallel direction of mass flow to heat flow is shown in the catalyst bed. The heat flow in this case is to be understood as that which flows from the catalyst bed to the wall having the heat transport medium space or in the reverse direction. The additional numbering of the drawing symbols has been omitted for clarity in the FIGS. 4–9. It can be seen that the FIGS. 4 and 5 are assigned to FIG. 1 and the FIGS. 6–9 are assigned to FIG. 2. In FIGS. 4 and 5 the heat flow moves both parallel and antiparallel to the mass flow; in FIGS. 6–9 this is either parallel or antiparallel.

Figure 10:
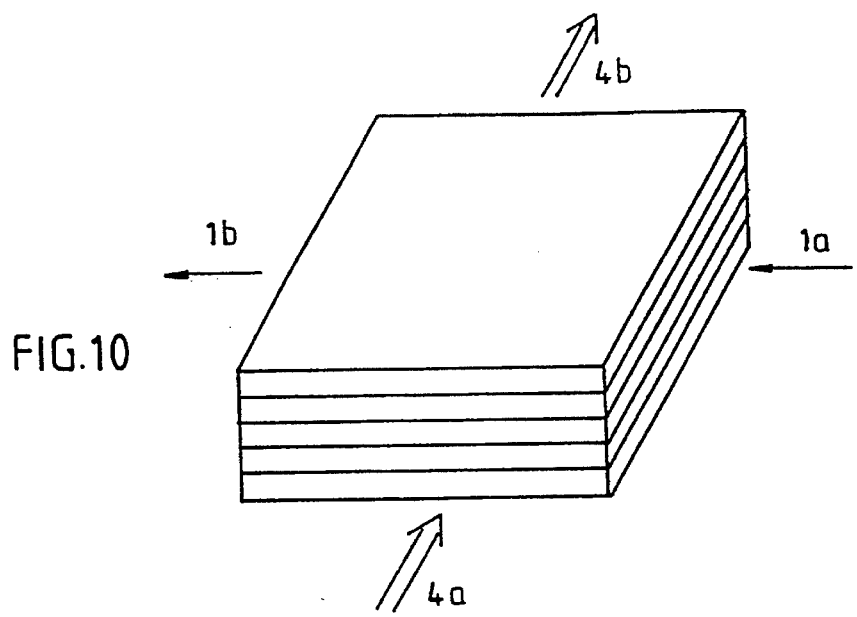
Figure 11A:
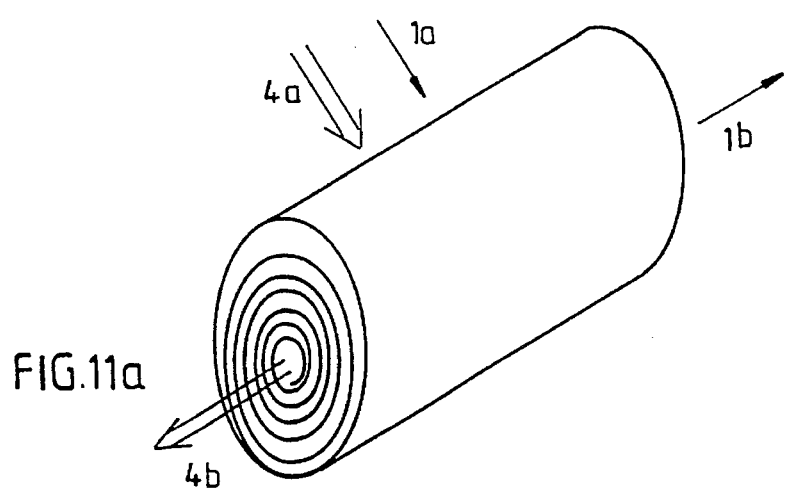
Figure 11B:
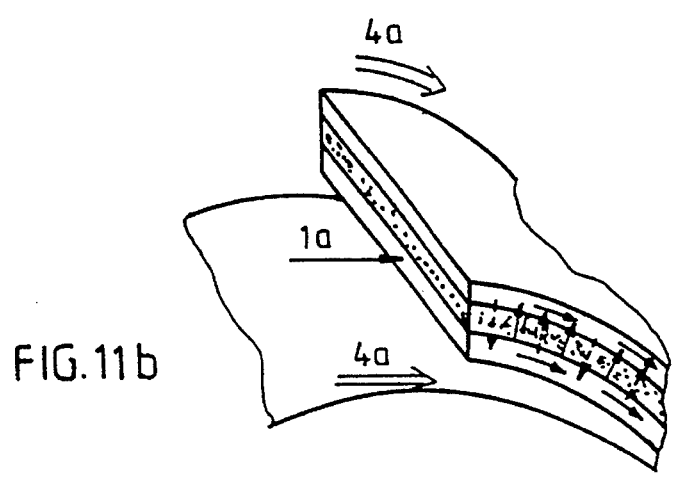
Figure 12:
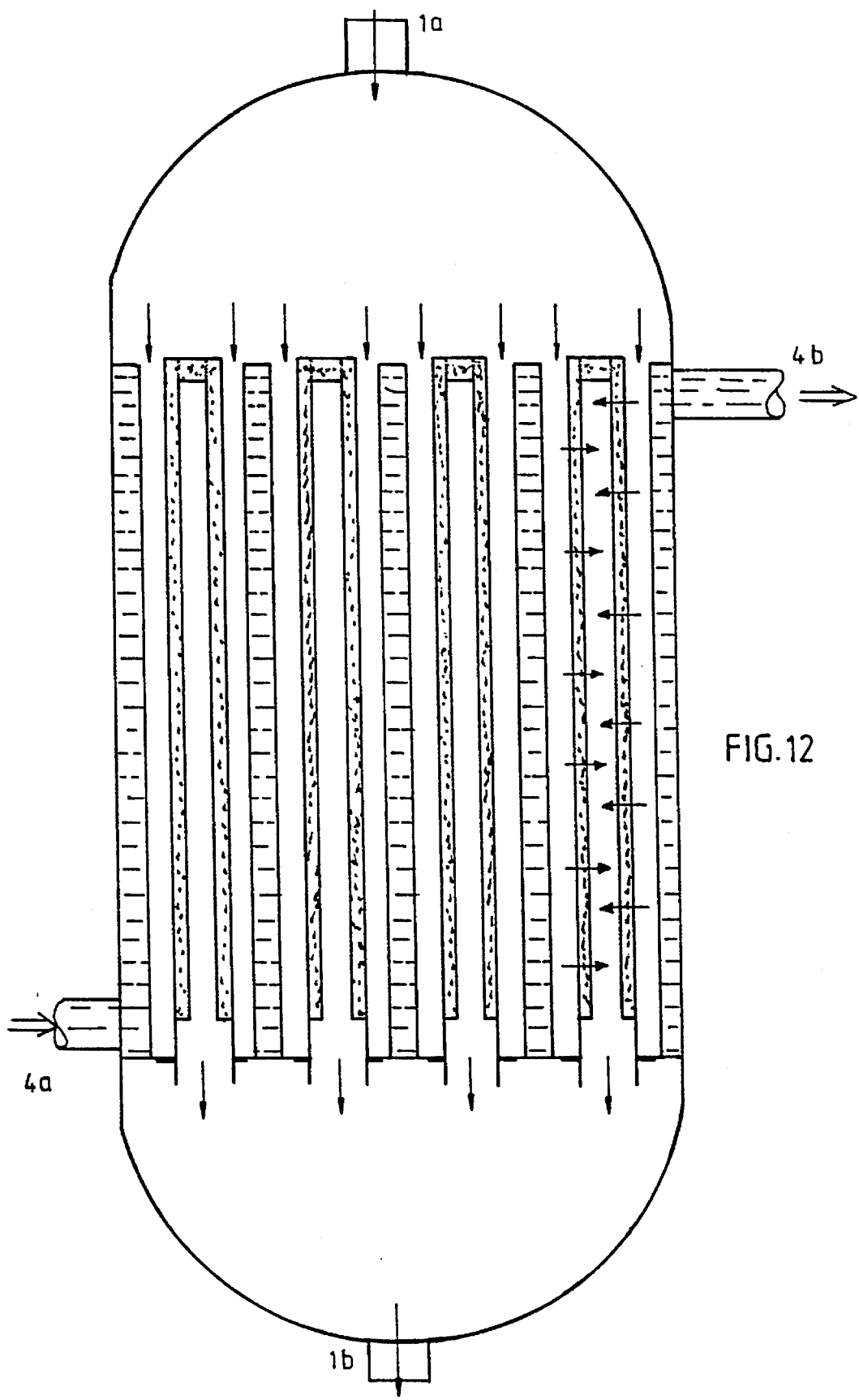

The catalyst bed can be designed to be one or more sheet-like layers. Thus, the sheet-like catalyst layers and the facing walls, regularly shaped in an identical manner, of the heat transport medium spaces can be combined (FIG. 10) in a package-like arrangement; however, the combination of sheet-like catalyst and heat transport medium space can also be arranged in a "rolled-up" cylindrical shape (FIG. 11a). If, in this case, in the overall arrangement mass flow and heat transport medium flow are also orthogonal to each other, this does not apply in the abovementioned manner individually to the catalyst bed, such as is shown in FIG. 11b; in FIG. 11b, the heat transport medium is guided in the direction of a spiral and thermostatted both on the starting material side and on the product side.

The FIGS. 12–15 show possible industrial embodiments in which tube elements are used in the manner of conventional tube-bundle reactors. FIGS. 16–19 show individual tube elements for such reactors which can be fitted into the reactor body by screwing, welding or another manner known in principle.

Figure 14:
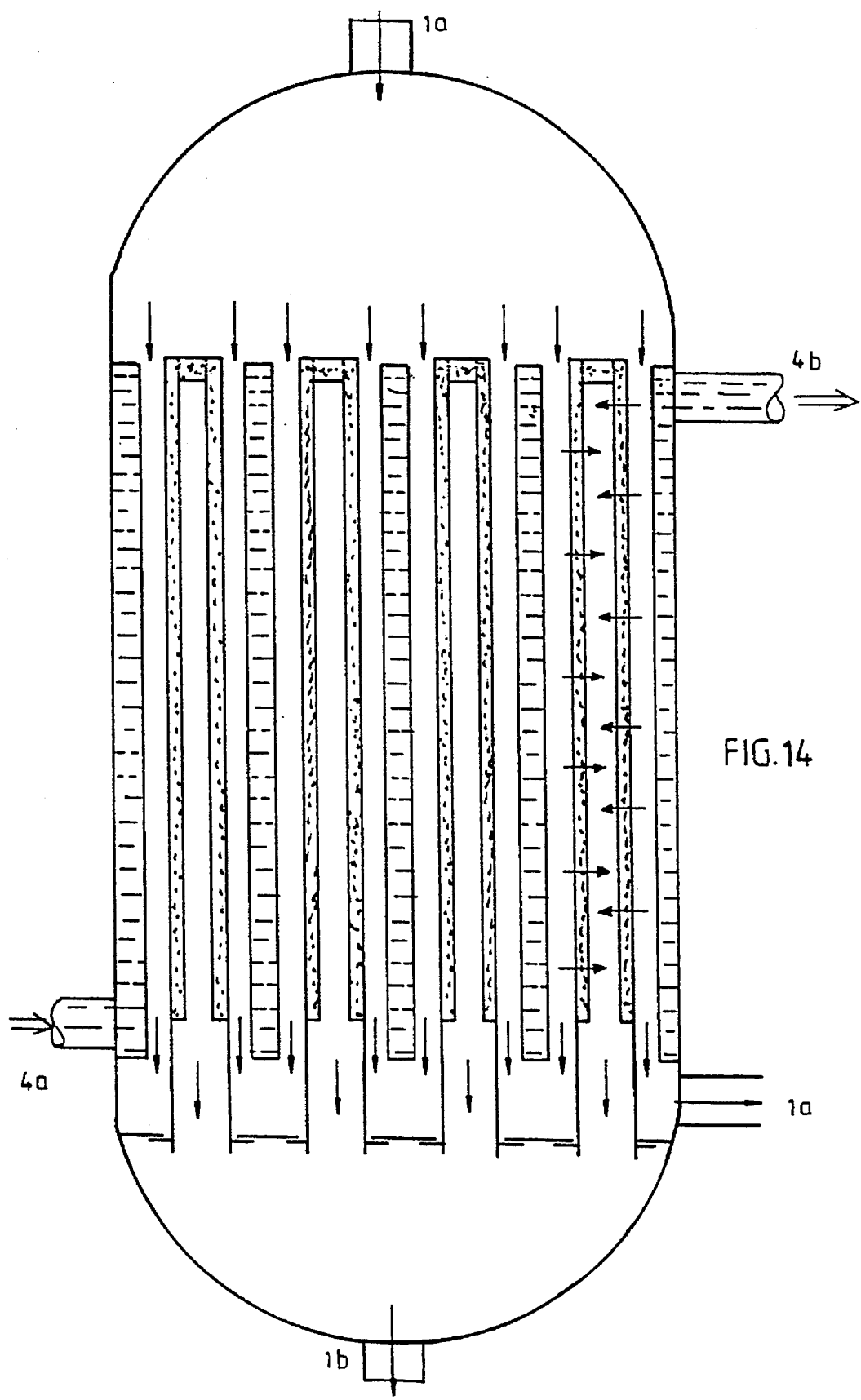
Figure 15:
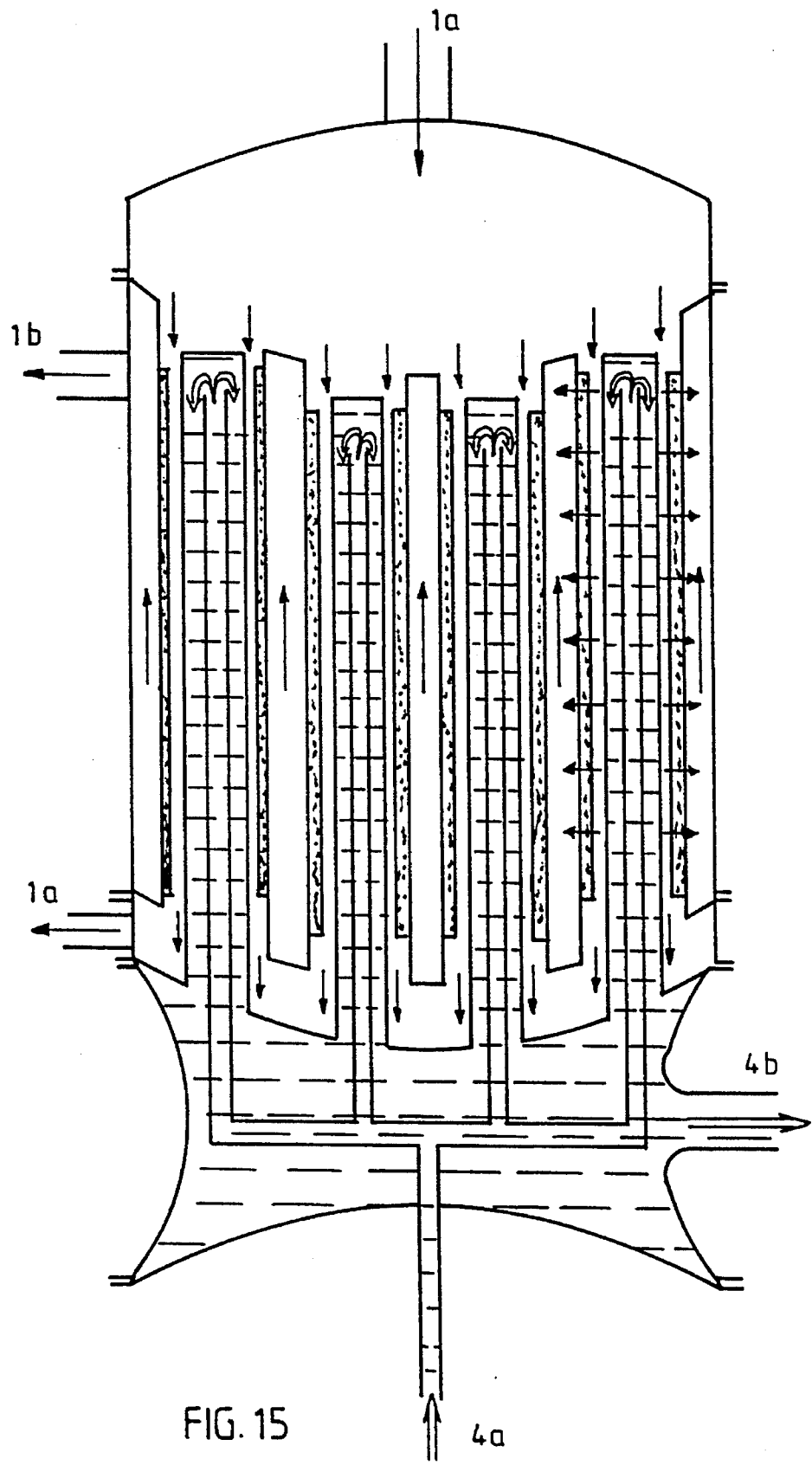
Figure 16:
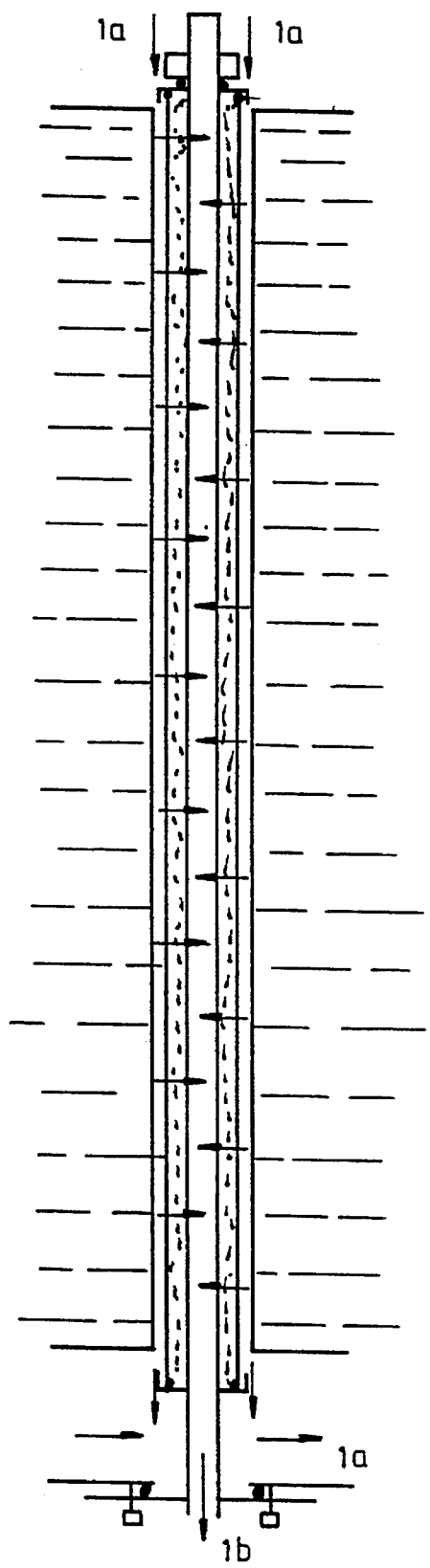
Figure 17:
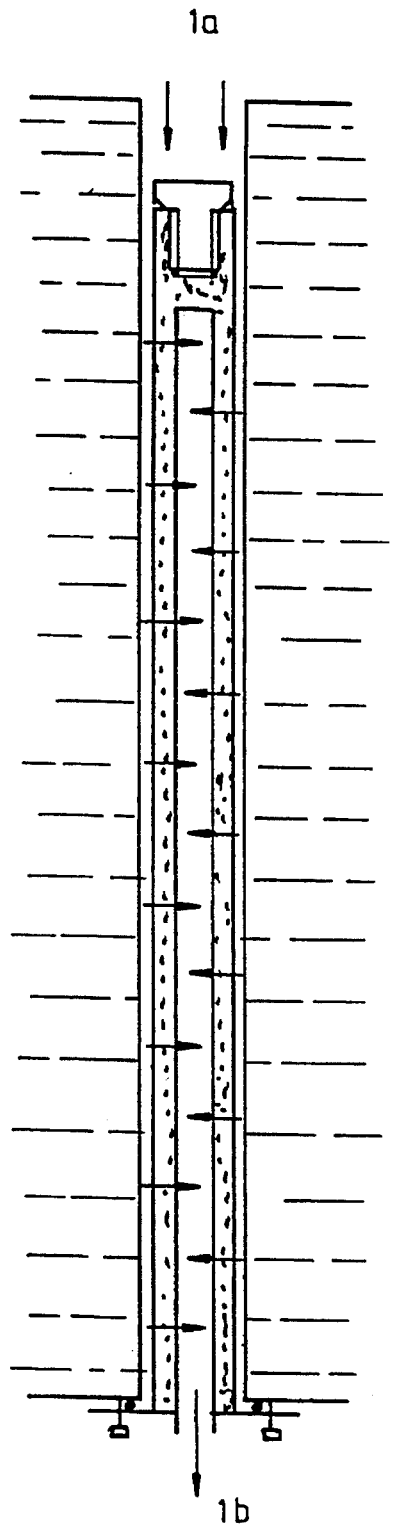

Industrial embodiments of the reactors according to the invention can also be designed for a partial circulation of the reaction partners around the reactor (recirculation) in such a manner that a part of the reactor discharge is withdrawn as the product stream which is fed to the further processing, while a further part of the reactor discharge is returned to the reactor inlet in order to be reused there to complete the reaction or to serve as an endogenous diluent for the starting materials. In a corresponding manner, a part of the starting materials which has not yet passed through the catalyst layer can also recirculate; the latter is indicated in FIGS. 14 and 15 on the basis of the reactors from FIGS. 12 and 13. The partial recirculation of the product stream and particularly of the starting material stream to the reactor inlet is suitable at the same time to increase the flow velocity of the starting material stream between the heat exchanger surface and the catalyst surface, the heat transfer between catalyst bed and thermostatting medium, or vice versa, being improved. The starting material recirculation is especially suitable for this as the starting material stream circulating along the entire "tube length" makes a constant addition to the starting material stream passing through the catalyst, which is not the case with the product recirculation and which leads to a particularly pronounced effect at the tube end.

For reactors having product-side thermostatting, if required, a product circulation stream corresponding to the abovementioned starting material circulation stream is to be installed which is not, however, directed through the catalyst, as described further above, but which, corresponding to the abovementioned starting material circulation stream, is fed to the product collection channels.

If required, all three variants to improve the heat transfer can be effected at the same time.

The exemplary embodiments shown additionally make clear that in the reactors according to the invention a uniform heat removal or supply is achieved over the entire heat exchange surface, a simpler reactor construction being made possible on the thermostatting medium side.

The reactors according to the invention are characterised in that the incoming starting material needs as large as possible a catalyst bed surface and at the same time as large as possible a surface is effected for the heat exchange. This means that for a given space-time load, a very low flow loading occurs and the catalyst is uniformly temperature-controlled. This further means, that in the reactors according to the invention, in contrast to the known reactors having continuous thermostatting, the heat flow, in relation to the mass flow, is directed through the catalyst in parallel, antiparallel or in parallel and antiparallel. In connection with this, the catalytically active beds in the reactors according to the invention have a particularly low extension in the direction of flow. It varies in the range 0.01–50 cm, preferably 0.02–20 cm, particularly preferably 0.05– 10 cm, highly particularly preferably 0.1–5 cm, extremely preferably 0.2–2 cm. The catalyst packing in the reactors according to the invention is bordered by porous walls which, as well as fixing the catalyst packing, have the task of guaranteeing the uniform flow through the catalyst bed over the entire surface. For this purpose, the resistance to flow of these walls and of the catalyst bed must exceed a certain minimum value which can easily be determined by those skilled in the art either experimentally or by calculation. The minimum resistance to flow of the catalyst beds including the porous gas distribution walls is generally to have values from 1 mbar to 10 bar, preferably from 2 mbar to 1 bar, particularly preferably from 5 mbar to 500 mbar.

The porous walls in the reactors according to the invention are preferably composed of sintered materials having an appropriate porosity, such as are known to those skilled in the art for gas distribution. Sintered metal shapes are particularly preferable because of their good thermal conductivity. In addition, perforated plate constructions or mesh fabric constructions can also be used. These must also comply with the requirements to distribute the starting material gas stream without relatively large local variations onto the catalyst and to ensure a uniform flow through the packing; for this purpose, a sufficient resistance to flow is again likewise required, which can also be at least partially produced by the catalyst packing. For this purpose, the catalyst material must be sufficiently fine-grained in order, with the low penetration depth, to ensure the required pressure drop in a sufficient depth. It is further understandable that the catalyst must have a sufficient flowability to ensure uniform packing in the filling process; thus, the catalyst material must not, for example, have a tendency to aggregation. The association between particle shape and particle size on the one hand and the resistance to flow of a packing made of such particles on the other is known to those skilled in the art and can be experimentally determined. The two walls serving to fix the catalyst packing and for gas distribution can also be replaced by a catalytically active shaped body, possibly in the form of a layer or built up from layers, which can be composed wholly or partially of sintered material, preferably sintered metal, which at the same time serves for gas distribution and as a support for the catalytically active material. Such a shaped body can be catalytically active in whole or in part. The principal methods for coating sintered materials with catalytically active particles are known to those skilled in the art (EP 416 710).

A further characteristic of the reactors according to the invention is, in addition, the fact that the heat flow must cross a small gas space section in order to pass from the gas distribution surface on the starting material side and/or product side to the particular surface in question which borders the thermostatting medium and is obviously impermeable to the mass flow; the same applies for a heat flow in the reverse direction from the thermostatting medium to the gas distribution surface.

When gases to be reacted which have a low thermal conductivity are used, it is expedient to design the length of the gas path between catalyst and the partition wall to the thermostatting medium shorter. Indeed, it is possible in principle, even with gases having poor thermal conductivity, to provide a long gas pathway and to effect the heat conduction by means of metal plate cooling structures which start from the partition surface to the thermostatting medium. However, such a construction is complicated and is therefore not preferred.

A further possibility for the utilisation of long pathways for the gases having poor thermal conductivity is the increase in flow velocity, as has already been described further above and can be effected by a partial circulation of the starting material and/or the product to the reactor entrance and/or of the product into the collection channels. The gap width which the heat flow has to bridge through the gas phase (distance between the catalyst bed and wall to the thermostatting medium) in the reactors according to the invention can be 0.1–10 cm, preferably 0.2–8 cm, particularly preferably 0.3–6 cm, very particularly preferably 0.4–4 cm.

The specific use of a resistance to heat flow determined by selection of the gap width of the gas space offers the possibility of establishing the temperature difference between the thermostatting medium and the catalyst in an expedient and desired range in the design of the reactor. Thus, it is possible, for example, in association with the extraordinarily uniform heat production over the entire exchanger surface, to establish an oil thermostatting in the temperature range expedient for the oil selected. This is of importance if with another reactor design, a conversion has to be made from an oil as heat transport medium to a salt melt which is more complicated to handle.

The temperature difference between the thermostatting medium and the catalyst surface can, in the reactors according to the invention, assume values from 2° to 250° C., preferably 5° to 200° C., particularly preferably 10° to 180° C. and very particularly preferably from 20° to 130° C.

The vector components of the flow velocity of the heat-transporting gases lying parallel to the gas distribution surface or product collection surface in the reactors according to the invention are established at values of 0–1000 m/seconds, preferably 0–100 m/seconds, particularly preferably 0–10 m/seconds. The lower value zero in this range denotes here the quantity that the said vector components assume at the end of the feed layers or at the beginning of the collection and discharge layers in the structures without circulation of starting material and/or of product.

The surface shape of the tubes and gas distribution elements can differ from a smooth surface to produce turbulence, that is can show, for example, ribs or similar additions.

For the reactor types which are thermostatted on one half, the reaction conditions applying are slightly to partly adiabatic, depending on the bed thickness, the thermal conductivity of the catalyst bed, the gas distribution system and the gas streams. More than 20%, preferably more than 40%, particularly preferably more than 60%, highly particularly preferably more than 80%, extremely preferably more than 90% of the heat of reaction is removed or supplied via the thermostatting medium (heat transport medium). To improve the heat capacity of the gas mixture to be reacted, to this, if required, can be added one or more additional heat transport medium components. These components preferably arise from the starting materials or products of the reaction.

For the reactor types having double-sided thermostatting, the relevant embodiment of the reactor is selected in such a manner that the amount of the temperature difference between the mean value of inlet and outlet temperature of the catalyst bed surface and the temperature of the catalyst bed interior at the hottest point (exothermic reaction) or at the coldest point (endothermic reaction) is between 1° and 300° C., preferably between 1° and 200° C., particularly preferably between 1° and 100° C., highly particularly preferably between 1° and 60° C., extremely preferably between 1° and 30° C.

The abovementioned temperature difference ranges likewise apply to the embodiments thermostatted on one half.

In accordance with the prior art, a reactor according to the invention can be furnished with a pressure-resistant casing, so that the reactions proceeding therein can proceed at superatmospheric pressure or subatmospheric pressure.

In contrast to the known pressure reactors, in the reactors according to the invention it is possible to restrict the high pressure part to the feed system and the actual catalyst bed, by using outlet sintered bodies having an appropriate resistance to flow.

Such a construction offers the advantage that the high pressure space which is expensive in terms of construction can be kept small.

Figure 13:
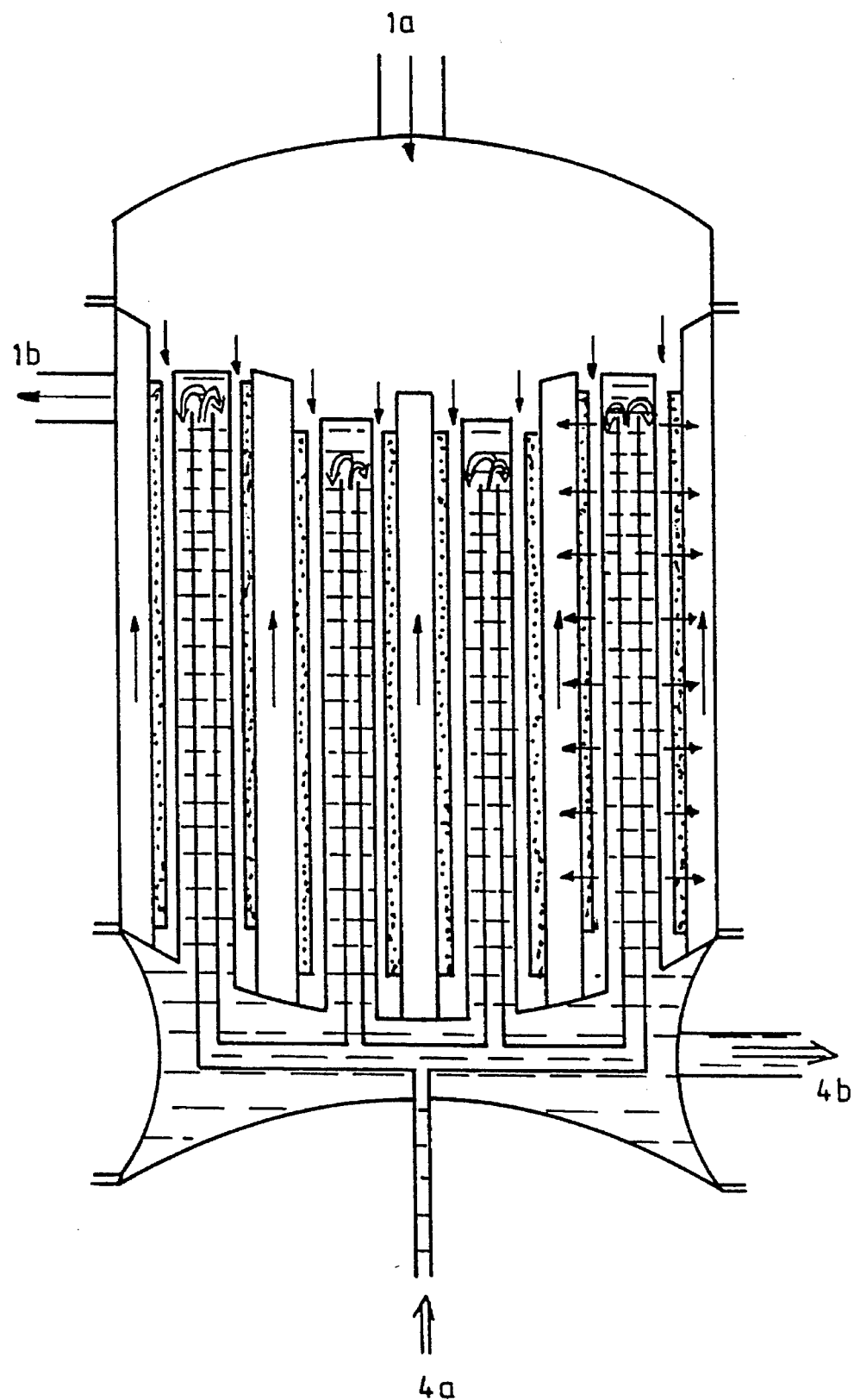

Preference is given in this case, for example, to structures such as are shown in FIGS. 13 and 15.

For high pressure reactions having only partial conversion and a corresponding recycling of starting material, it is to be emphasised with the reactors according to the invention that the system can be optimised to a very low resistance to fluid flow with, at the same time, very good thermostatting, which has low pump outputs to return the compressed viscose gases as a consequence.

On the basis of a hollow cylinder construction, the number of the internals in such a reactor type and their dimensioning is to be considered below. The trend with conventional tube-bundle reactors, to convert to increasingly smaller built-in elements for better reaction control, whether it be to increasingly narrower tubes or increasingly shorter tubes, leads to an increase in the number of tubes. Industrial reactors of conventional construction not infrequently possess 10,000 tubes or more. In the short-tube reactor described in EP 244,632 already cited above, a quantity of 100,000 tubes would certainly be attained or exceeded. Using as example the tube-bundle reactors according to the invention having radial heat flow and mass flow (that is parallel or antiparallel or both parallel and antiparallel) it is to be made clear that using the reactor principle according to the invention, the trend to increasingly more numerous built-in elements has been broken. The comparison reactors to be considered are conventional tube bundle reactors having tube internal diameters of 1.5 or 2.5 cm. Table 1 shows the number of tubes of reactors according to the invention having a bed thickness of 1 cm and different tube diameters, when for the same space time loading and tube length, the conventional comparison reactors accommodate 10,000 tubes.

TABLE 1

Number of tubes of the tube-bundle reactors according to the invention in comparison to conventional tube-bundle reactors (Ø denotes diameter)

| Conventional tube-bundle reactors | Tube-bundle reactors according to the invention | | |
|---|---|---|---|
| | Ø = 40 | Ø = 20 | Ø = 10 cm |
| (10,000 tubes) | Number of tubes | | |
| Ø = 1.5 cm | 145 | 294 | 625 |
| Ø = 2.5 cm | 400 | 833 | 1666 |

Reactor tubes according to the invention having 40 cm φ can, for example, be those as in FIG. 18, the thin-layer catalyst bed being designed as a hollow tube and being screwed over a stopper for the circulation of the heat transport medium. Reactor tubes according to the invention having 10 cm φ are, for example, those of the type shown in FIG. 16, the thin-layer catalyst layer again being designed as a hollow tube, but in contrast to FIG. 18 being screwed into a corresponding recess within the volume through which the heat transport medium flows. Generally and independently of the exemplary data in the above Table 1, the tube diameters of the tubebundle reactors according to the invention having a hollow cylindrical catalyst arrangement are in the range from 5–200 cm, preferably from 7–100 cm, particularly preferably from 10–50 cm. The tube lengths vary within the range 1–40 m, preferably 2–20 m, particularly preferably 3–10 m. Following known types, the catalyst hollow cylinders according to the invention are generally also used in a plurality thereof as a relatively large unit, for example as a tube bundle.

The reactors according to the invention can in principle be used for any heterogeneously catalysed gas-phase reaction. However, they are particularly suitable for reactions which tend to give a pronounced hot-spot in conventional tube reactors, furthermore for reactions which must proceed in a relatively restricted temperature range, furthermore for reactions whose catalyst is quickly overloaded and then has a tendency to side reactions, furthermore for reactions which demand a precisely defined residence time, since they otherwise have a tendency to secondary reactions and finally for reactions which require extremely short residence times with, at the same time, good cooling, because they proceed extremely quickly and then have a tendency to secondary reactions.

The by-products and secondary reaction products of a gas-phase reaction, which arise as a result of the temperature, the catalyst loading or the residence time, can contribute decisively to the deactivation of the catalyst as a result of coking. This is fundamentally a similarly undesirable deactivation as the catalyst deactivation as a result of pure temperature overload. Therefore, the reactors according to the invention are particularly highly suitable if long catalyst operating lives are required, whether it be because the catalyst cannot be regenerated or because the industrial reaction must require as little maintenance as possible. The precise reaction conditions and the particularly low tendency to deactivation of the catalysts in the reactors according to the invention can be explained by the low penetration depth of the catalyst beds and in that the poorly volatile coke precursors can leave the catalyst bed before they become stationary.

Examples of reactions which can be carried out particularly expediently in the reactors according to the invention are, without this listing being exhaustive: dehydrogenations, for example, of cyclohexylidene-aniline to give diphenylamine and of cyclohexenyl-cyclohexanone to give o-phenylphenol; hydrogenations, for example, of nitrobenzene to give aniline and of phenol to give cyclohexanone; oxidative alcohol dehydrogenations, for example, of 3-methyl-3-buten-1-ol to give 3-methyl-2-buten-1-al; selective oxidations of hydrocarbons, for example, of n-butane to give maleic anhydride, of oxylene to give phthalic anhydride and of propene to give acrolein or acrylic acid and alkylations and halogenations.

The extraordinarily successful functioning of the reactors according to the invention is surprising, since according to the prior engineering art, radial reactors can only be thermostatted in a very complicated manner, if at all (Chem. Tech. 30. (1978), 74). This prejudice in the context of the prior engineering art is principally based on the poor thermal conductivity of gases. The reactors according to the invention should, according to this prior art, only be suitable for reactions to be carried out under adiabatic conditions.

EXAMPLE 1

Preparation of the catalyst for the dehydrogenation of cyclohexylidene-aniline to give diphenylamine A liter of aluminium oxide support, composed of spheres having a diameter of 2.0 to 3.0 mm, having a BET surface area of 74 $m^2$/g, an absorption capacity of 54 ml of $H_2O$ per 100 g of support and a bulk density of 717 g/l was impregnated with 387 ml of an aqueous NaOH solution which contained 13.5 g, corresponding to 0.34 gram equivalents, of NaOH. The solution was completely absorbed in the support within 2 minutes. The moist support was packed into a vertical glass tube of approximately 2 l capacity and was then treated with warm air of 105° to 120° C. at a rate of 20 $m^3$/h from bottom to top. It was dried to constant weight of the support, which was the case after 30 minutes. The residual moisture content of the dried support, after cooling to room temperature, was 0.25% by weight, corresponding to approximately 0.47% of the absorption capacity.

The pretreated, dry support was soaked with an aqueous sodium tetrachloropalladate solution, containing 18 g of Pd, corresponding to 0.216 gram equivalents, in accordance with its absorption capacity and allowed to stand for 15 minutes. The catalyst was then washed in a flowing stream of distilled water until no further sodium ions and chloride ions were detectable in the washing water, which was the case after 12 hours.

The subsequent drying took place in a warm air stream, as previously described in the drying of the support. The catalyst thus prepared contained, calculated as the metal, 18 g of Pd per liter of support (1.555% by weight).

EXAMPLE 2

Dehydrogenation of cyclohexylidene-aniline to give diphenylamine in a tube reactor (comparison example)

A 15 cm-long catalyst packing was introduced into the centre of an oil-thermostatted glass tube reactor (length=40 cm, internal diameter=2.3 cm).

The catalyst packing was located between two packings of 5 mm glass beads. The oil jacket of the reactor was connected to a high temperature oil thermostat and the catalyst was heated in a hydrogen stream to 250° C. The hydrogen stream was replaced by a nitrogen stream and the temperature of the oil Jacket was increased to 320° C. At a loading of 0.3 g/ml.h (based on the catalyst packing volume), cyclohexylidene-aniline in a nitrogen stream was passed over the catalyst (1 l of $N_2$/g of cyclohexylidene-aniline). At 100% conversion, diphenylamine, at 95% selectivity, left the reactor in a gaseous state in a nitrogen/hydrogen mixture.

The main reaction zone could be recognised in the reactor bed by a temperature trough. This temperature trough moved in the course of time from the catalyst head in the direction of the catalyst end. After approximately 100 to 150 hours, the progressive catalyst deactivation became noticeable by a rapidly increasing cyclohexylideneaniline content in the product mixture.

EXAMPLE 3

Dehydrogenation of cyclohexylidene-aniline to give diphenylamine in a hollow cylindrical tube reactor according to the invention The reactor comprised an oil-thermostatted glass tube (length 62 cm, internal diameter 4.9 cm). A tube made of sintered glass material was located concentrically to this glass tube in the interior of the thermostatted glass tube. This tube (length=15 cm, diameter=2.0 cm, porosity 3) was sealed by fusion at the top end and at the bottom end was fused onto an evacuated jacketed glass tube having a tapered ground glass joint (standard ground joint NS29) (inner glass tube of diameter 2.4 cm, outer glass tube of diameter 3.8 cm); the space between the inner and outer glass tube was evacuated. The product gas was conducted away through the inner glass tube. The outer glass tube had a length of 25 cm, measured from the NS29 ground joint to the bottom of the thermostatted glass tube. At the end of the thermostatted glass tube, the outer glass tube sealed to the thermostatted glass tube in a gas-tight manner. Concentrically to the inner sintered glass tube, there was located a further sintered glass tube in the interior of the oil-thermostatted glass tube (length=15 cm, internal diameter=3.2 cm, wall thickness=2 mm, porosity 3). This sintered glass tube was fused at the bottom to an NS29 ground glass joint socket, which was seated in a gas-tight manner on the ground glass joint cone of the vacuum Jacketed tube. The outer sintered glass tube was fused at the top to a 10 cm-long glass tube having an NS29 socket. An approximately 10 cm-long evacuated ground glass joint stopper was seated in a gas-tight manner in this socket.

The catalyst packing was located between the outer and inner sintered glass tube.

The oil jacket of the reactor was connected to a high temperature oil thermostat and the catalyst was heated in a hydrogen stream to 250° C. The hydrogen stream was replaced by a nitrogen stream and the temperature of the oil Jacket was increased to 320° C. At a loading of 0.3 g/ml.h (based on the catalyst volume), cyclohexylideneaniline was passed in a nitrogen stream from the outside to the inside over the catalyst (1 l of $N_2$/g of cyclohexlidene-aniline). At 100% conversion, diphenylamine left the reactor in the gaseous state at 95% selectivity in a nitrogen/hydrogen mixture. The trial was completed after 1000 hours running time without significant changes in the, product composition (that is without catalyst deactivation).

EXAMPLE 4

Preparation of the catalyst for the reduction of nitrobenzene to give aniline

One liter of an α-aluminium oxide support in bead form having diameter 3 to 4 mm, a BET surface of 9.8 $m^2$/g, an absorption capacity of 45.1 ml of water per 100 g of support and a bulk density of 812 g/l was impregnated with 366 ml of an aqueous solution containing 10.8 g, corresponding to 0.27 gram equivalents, of NaOH. The solution was completely absorbed by the support in the course of a few minutes. The moist support was packed into a vertical glass tube of approximately 2 l capacity and was dried in a warm air stream at 120° C. at an air flow rate of 25 $m^3$ (S.T.P.) of air per hour. The drying time until constant weight was about 30 minutes. The residual moisture content, after cooling to room temperature, was approximately 0.9% of the absorption capacity of the support.

The thus pretreated dry support, in accordance with its absorption capacity, was soaked with 366 ml of an aqueous sodium tetrachloropalladate(II) solution which contained 9 g of palladium, corresponding to 0.169 gram equivalents, and allowed to stand for 15 minutes. To reduce the palladium compound deposited on the support to metallic palladium, the support was coated in a beaker with 400 ml of a 10% strength aqueous hydrazine hydrate solution and allowed to stand for 2 hours. The catalyst was then washed in a flowing stream of distilled water until no ions of the compounds used in the catalyst preparation could be detected any longer in the washing water, which was the case after 10 hours.

The subsequent drying was carried out in the warm air stream as described previously for the drying of the support. The catalyst thus prepared contained 9 g of palladium per liter of support.

The Pd-containing catalyst was then soaked with 366 ml of an aqueous solution containing 9 g of vanadium in the form of vanadyl oxalate. The drying of the Pd catalyst impregnated with vanadyl oxalate was carried out analogously to the drying of the support in the warm air stream at 120° C. The subsequent decomposition of the vanadyl oxalate was carried out in the course of 6 hours at 300° C.

After this treatment the catalyst was soaked with 366 ml of an aqueous solution containing 3 g of lead in the form of lead acetate. The catalyst impregnated with lead acetate was filled, in the wet state, into a tube reactor and dried in the course of the heat-up period of the heat transport medium.

The activation of the catalyst was carried out in the hydrogen stream at the temperature of the heat transport medium which was 280° C. The finished catalyst contained, calculated as the metal, 9 g of palladium, 9 g of vanadium and 3 g of lead per liter of support.

EXAMPLE 5

Hydrogenation of nitrobenzene in a tube reactor (comparison example)

A 200 cm-long oil-thermostatted metal tube reactor was furnished with a 150 cm-long catalyst packing (diameter= 2.3 cm). At an oil temperature of 200° C., a hydrogen stream was passed over the catalyst (594.9 l (S.T.P.)/hour), the oil temperature was increased to 270° C. and a catalyst loading of 0.5 g of nitrobenzene per ml of catalyst and hour was established (loading=0.5 g/ml h, $H_2$ excess 250%).

In the vicinity of the catalyst top, a hot zone having a temperature of approximately 450° C. formed which moved with approximately constant speed in the direction of the catalyst end.

After about 1000 hours of running time, this zone reached the catalyst end whereupon, with rapidly increasing intensity, nitrobenzene was to be detected in the product gas mixture. Before the progressive deactivation reached the catalyst end, at 100% conversion, aniline was formed with a selectivity better than 99.5%.

EXAMPLE 6

Hydrogenation of nitrobenzene in a short-tube reactor (comparison example)

A 15 cm-long catalyst packing was placed in the centre of the glass reactor described in Example 2. After the activation in the hydrogen stream, nitrobenzene was passed over the catalyst at an oil bath temperature of 220° C. at a loading of 0.5 g/ml h at a hydrogen excess of 250%. A hot zone formed on the catalyst having a maximum temperature of approximately 360° C. This hot zone moved, with flattening, towards the catalyst end. After approximately 1000 hours of running time, nitrobenzene began to leave the reactor with the product gas mixture. Before the deactivation reached the catalyst end, aniline was formed at 100% converson with a selectivity of better than 99.5%.

EXAMPLE 7

Hydrogenation of nitrobenzene in a hollow cylindrical tube reactor according to the invention The hollow cylinder reactor described in Example 3 received in exchange a different vacuum Jacket insert with fused-on sintered glass hollow cylinder. Length of the sintered glass tube fused on at the top 15 cm, diameter 1.2 cm. The bed thickness to be flowed through radially thus increased from 6 mm to 10 mm. The space between the sintered glass tubes was filled with catalyst.

As in Example 5 and Example 6, the catalyst, after a preliminary reduction at 220° C. oil bath temperature, was operated at a loading of 0.5 g of nitrobenzene per ml of catalyst and hour at 250% hydrogen excess. In the interior of the inner sintered glass tube, a temperature of 320° C. was measured with the aid of a temperature sensor. The trial was completed after 4000 hours running time without significant catalyst deactivation. During this time period, nitrobenzene was converted to 100% and aniline was formed with more than 99.8% selectivity.

EXAMPLE 8

Hydrogenation of nitrobenzene in a hollow cylinder reactor (comparison example)

The trial of Example 7 was repeated at 320° C. oil temperature. The outlet temperature of the product gas mixture in the interior of the reactor was 430° C. After 600 hours of running time, product composition and outlet temperature were unchanged (conversion 100%, selectivity >99.8%); only after a running time of 800 hours was an initial catalyst deactivation demonstrated.

What is claimed is:

1. In a reactor for the continuous reaction of gaseous substances comprising a plurality of fixed beds of catalyst and means for directing a gas through said fixed beds of catalyst and heat transfer means for transferring heat to or from said gas, the improvement wherein each of said catalyst beds is arranged in a sheet configuration having a thickness of from 0.05 to 10 cm and is contained between two surfaces, each of said surfaces comprises a covering that is perforated or porous sufficiently to permit the passage of a gas, but not the catalyst, perpendicularly therethrough, and wherein said heat-transfer means comprises a plurality of heat transfer surfaces of a sheet configuration similar to that of said catalyst beds, each of which is positioned in substantial alignment with and spaced apart from one of said two surfaces covering said plurality of catalyst beds a distance of from about 0.1 to 10.0 cm, to form thereby a space between one of said two surfaces covering said plurality of catalyst beds and one of said plurality of heat transfer surfaces, with the side of the heat transfer surface opposite the catalyst bed being in contact with a heat transfer medium, whereby a gas fed to said reactor will pass through at least one of said spaces and come into contact with at least one of said heat transfer surfaces either before passing through said catalyst bed, after passing through said catalyst bed, or both, whereupon heat may be transferred between said gas and said catalyst, as well as between said gas and said heat transfer surface and wherein said catalyst bed, including said surface covering, has a minimum resistance to fluid flow of 2 mbar to 10 bar.

2. The reactor of claim 1, wherein the catalyst bed has a thickness of 0.1–5 cm.

3. The reactor of claim 2, wherein the catalyst bed has a thickness of 0.2–2 cm.

4. The reactor of claim 1, wherein the distance between said catalyst bed and said heat transfer surface is 0.2–8 cm.

5. The reactor of claim 4, wherein the distance between said catalyst bed and said heat transfer surface is 0.3–6 cm.

6. The reactor of claim 5 wherein the distance between said catalyst bed and said heat transfer surface is 0.4–4 cm.

7. The reactor of claim 1, wherein the catalyst bed has a minimum resistance to fluid flow of 2 mbar to 1 bar.

8. The reactor of claim 7, wherein the catalyst bed has a minimum resistance to fluid flow of 5 to 500 mbar.

9. The reactor of claim 1, wherein said plurality of fixed-beds of catalyst arranged in said sheet-like configuration are each formed as a hollow cylinder sealed on one end and having a diameter of 5–200 cm.

10. The reactor of claim 9, wherein 61 said layers of the catalyst bed are formed as hollow cylinders having diameters of 7–100 cm.

11. The reactor of claim 9, wherein 62 said layers of the catalyst bed are formed as hollow cylinders arranged as a plurality of them as a tube bundle.

12. The reactor of claim 11, wherein the hollow cylinders are arranged as a tube bundle.

\* \* \* \* \*

UNITED STATES PATENT AND TRADEMARK OFFICE
CERTIFICATE OF CORRECTION

PATENT NO. : 5,484,576
DATED : January 16, 1996
INVENTOR(S) : Langer, et al.

It is certified that error appears in the above-indentified patent and that said Letters Patent is hereby corrected as shown below:

Col. 14, line 43, after "wherein" delete "61" insert —said—
Col. 14, line 46, after "wherein" delete "62" insert —said—

Signed and Sealed this

Tenth Day of September, 1996

Attest:

BRUCE LEHMAN

Attesting Officer     Commissioner of Patents and Trademarks